US005759522A

United States Patent [19]

Ulmer et al.

[11] Patent Number: 5,759,522

[45] **Date of Patent: *Jun. 2, 1998**

[54] INNOVATIVE-TYPE HAIR SPRAY CONCENTRATE CAPABLE OF DELIVERING REDUCED VOC SPRAY PARTICLES

[75] Inventors: Herbert Ulmer, Hoboken; Colleen M. Rocafort, Lake Hiawatha, both of N.J.

[73] Assignee: ISP Investments Inc., Wilmington, Del.

[ * ] Notice: The term of this patent shall not extend beyond the expiration date of Pat. No. 5,614,173.

[21] Appl. No.: 740,344

[22] Filed: Nov. 7, 1996

Related U.S. Application Data

[63] Continuation-in-part of Ser. No. 569,809, Dec. 8, 1995, Pat. No. 5,614,173.

[51] Int. Cl.[6] .......... A61K 7/11

[52] U.S. Cl. .......... 424/47; 424/78.02; 424/70.11; 424/DIG. 1; 424/DIG. 2; 514/957

[58] Field of Search .......... 424/47, DIG. 1, 424/DIG. 2, 78.02, 70.11; 514/957

[56] References Cited

U.S. PATENT DOCUMENTS

| | | | |
|---|---|---|---|
| 4,897,262 | 1/1990 | Nandagiri et al. | 424/70.11 |
| 5,021,238 | 6/1991 | Martino et al. | 424/DIG. 2 |
| 5,094,838 | 3/1992 | Benson et al. | 424/DIG. 1 |
| 5,126,126 | 6/1992 | Varaprath et al. | 424/47 |
| 5,176,898 | 1/1993 | Goldberg et al. | 424/47 |
| 5,614,173 | 3/1997 | Ulmer et al. | 424/47 |

OTHER PUBLICATIONS

Martino, G.T et al. (1992). Spray Technology & Marketing, Mar. Issue, pp. 34–39.

Johnsen, M.A. (1992). Spray Technology & Marketing, Jun. Issue, pp. 32–40.

*Primary Examiner*—Raj Bawa
*Attorney, Agent, or Firm*—Walter Katz; Marilyn J. Maue; William J. Davis

[57] ABSTRACT

An innovative-type hair spray concentrate of defined Brookfield viscosity and solids content which is capable of delivering reduced VOC spray particles of acceptable quality under the Innovative Product Clause Regulations in combination with a suitable restricter valve and actuator system. The concentrate includes a fixative which is the half-ester of a copolymer of maleic anhydride and methyl vinyl ether having a weight average molecular weight of about 40,000 to about 70,000, which provides advantageous physical and use performance properties.

3 Claims, 1 Drawing Sheet

Brookfield Viscosity of the Invention in Various VOC Systems:
(1) 55% VOC, (2) 80% VOC and (3) Anhydrous System

FIGURE
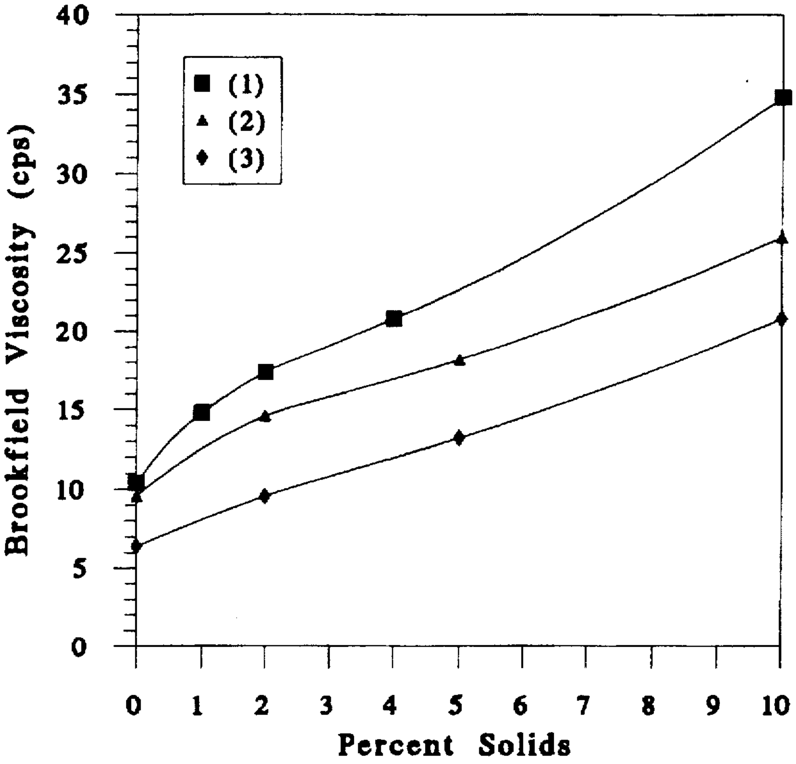
Brookfield Viscosity of the Invention in Various VOC Systems:
(1) 55% VOC, (2) 80% VOC and (3) Anhydrous System

INNOVATIVE-TYPE HAIR SPRAY CONCENTRATE CAPABLE OF DELIVERING REDUCED VOC SPRAY PARTICLES

CROSS-REFERENCE TO RELATED U.S. PATENT APPLICATIONS

This application is a continuation-in-part of U.S. patent application Ser. No. 08/569,809, filed Dec. 8, 1995, now U.S. Pat. 5,614,173, issued Mar. 25, 1997 by the same named applicants as herein.

BACKGROUND OF THE INVENTION

1. Field of the Invention

This invention relates to an innovative-type hair spray concentrate, and, more particularly, to such product having a defined Brookfield viscosity and solids content which is capable of delivering reduced VOC spray particles of acceptable quality which provides advantageous performance characteristics for the user.

2. Description of the Prior Art

Copolymers of maleic anhydride and methyl vinyl ether, in the form of the $C_1$–$C_5$ alkyl half-ester, e.g. the ethyl half-ester, have been used extensively as a film-forming resin or fixative in hair spray compositions. Generally such ester copolymers have been prepared by polymerization of the monomers in benzene or acetone solution in the presence of a free radical polymerization initiator followed by esterification. See Brit. Pats. 863,379; 1,233,468 and 712,220; Ger. Pat. 540,101; and U.S. Pat. Nos. 2,047,398; 4,908,413; 4,939,198; 5,139,034; and 5,223,567.

Such ethyl half-esters of copolymers of maleic anhydride and methyl vinyl ether (Gantrez® ES-225), also may be prepared in acetone according to the free radical polymerization process using decanoyl peroxide as the polymerization initiator as described by Zamora et al., in U.S. Pat. No. 5,223,567. These copolymers, supplied by International Specialty Products, Inc. as a 50% solids solution in ethanol, have very high weight average molecular weights, in the order of 85,000 to 1 million.

Goertz et al., in U.S. Pat. No. 4,908,413, described the preparation of ethyl half-ester copolymers of maleic anhydride and excess methyl vinyl ether by thermal polymerization of the precharged monomers in acetone, followed by a second phase free radical polymerization. Esterification was carried out in ethanol in the presence of an esterification catalyst such as p-toluenesulfonic acid. However, the alcoholic solutions of such copolymers were considered as being only equivalent in their physical properties and performance characteristics to the corresponding ones obtained by previous processes. The weight average molecular weights of these copolymers, too, were excessively high, about 100,000 or above.

Recent governmental legislation has required that hair spray compositions contain only 80% or less volatile organic compounds (VOCs). Accordingly, it has been necessary for formulators of hair spray products to substitute water for much of the ethanol solvent presently used to dissolve the hair fixative resin. However, an increase in the water content of the product creates some significant problems, including:

A decrease in resin solubility

An increase in solution viscosity

An increase in spray particle size causing a poorer spray pattern

An increase in dry and tack times

A decrease in high humidity curl resistance (hold)

In aerosol formulations, the presence of water creates two additional problems:

Can corrosion

Solvent-propellant incompatibility.

An alternative approach to reduced VOC hair spray compositions is found in the "Innovative Product Clause" (IPC) in the governmental regulations. This clause allows for any VOC level in the formulation provided the quantity of VOC's emitted from such formulation over a given time is equal to or less than that emitted by a product of similar efficacy which is in direct compliance with the 80% or 55% VOC provisions of the statute. Such Innovative Products can use compressed air to deliver the resin to the hair, i.e. an innovative-type pump spray composition; or with a propellant, i.e. an innovative-type aerosol spray, as the delivery system. In operation, restrictive valving, coupled with a high solids formulation, results in deposition of identical amounts of polymer as achieved by standard 80% or 55% VOC hair spray compositions but at a lower overall rate of VOC emissions.

Accordingly, it is an object of this invention to provide an innovative-type hair spray concentrate which meets the IPC regulations, and which provides acceptable spray particles and advantageous user performance properties.

These and other objects and features of the invention will be made apparent from the following more detailed description of the invention.

SUMMARY OF THE INVENTION

What is described herein is an innovative-type aerosol hair spray concentrate, of defined Brookfield viscosity and solids content, capable of delivering reduced VOC spray particles over a given period of time, comprising, by weight, (a) about 5 to about 25% of the ethyl or butyl half-ester copolymer of maleic anhydride and methyl vinyl ether, having a low weight average molecular weight of about 40,000 to about 70,000, (i) optionally neutralized in an amount up to about 25 mole %, (b) about 40 to about 80% ethanol, (c) 0 to about 10% water, and (d) about 15 to about 40% propellant;

the hair spray concentrate having a Brookfield viscosity of about 15 to about 30 cps.

In cooperation with a suitable restricter valve to slow the rate of spray of the concentrate from the can, the concentrate of the invention will deliver acceptable spray particles at a suitable rate to satisfy the IPC regulations relating to 80% VOC and 55% VOC emissions from hair spray products.

IN THE DRAWINGS

The FIGURE is a plot of Brookfield viscosity vs. percent solids for concentrates of the invention at various VOC levels.

DETAILED DESCRIPTION OF THE INVENTION

What has been provided herein is a high solids hair spray fixative concentrate containing an alkyl half-ester of maleic anhydride and methyl vinyl ether copolymer which has a predetermined and advantageous low weight average molecular weight. This concentrate will satisfy the IPC regulations for reduced VOC hair spray in pump or aerosol systems, including the 80% or 55% VOC formulation regulations.

In this invention, such ester copolymers of relatively low weight average molecular weight, particularly about 40,000 to about 70,000, possess sufficient mechanical integrity, including strength, coatability and adhesion, to adequately hold the hair at a normal solids level of about 5% solids. In contrast, other known polymers for fixative use, at similar molecular weights, experience a substantial reduction in mechanical integrity in use.

The polymer system of the present invention also possesses a desired low solution Brookfield viscosity in the concentrate formulation, particularly about 15 to about 30 cps. At this level it may be sprayed acceptably at a reduced rate to satisfy an 80% VOC or 55% VOC emission under the IPC regulation.

The copolymers of this invention are made using suitable initiators such that their solutions and hair spray compositions therewith also will have advantageous physical and performance properties as compared to hair spray compositions made with commercial Gantrez® copolymer solutions.

In particular, in contrast to presently available Gantrez®, the copolymers of this invention have a low weight average molecular weight of about 40,000 to about 70,000, and a narrow polydispersity or molecular weight distribution, so that the hair spray concentrate has a desirable low Brookfield viscosity of about 15 to about 30 cps, at a solids content of about 5 to about 25%. This concentrate is suitable for forming advantageous spray particles of small size, in both pump and aerosol systems. With these copolymer solutions and compositions, the consumer also can experience an exceptional holding power on the hair, as well as advantageous tack and dry times.

The copolymers of this invention can be prepared using either azo or peroxide-type initiators to initiate the polymerization reaction. However, azo initiators, as described in copending U.S. patent application Ser. No. 08/569,809, filed Dec. 8, 1995, are preferred because the resultant polymer systems generally possess a narrower molecular weight distribution than similar systems prepared with a peroxide initiator.

The azo initiators also are advantageous because their decomposition fragments are compatible with the polymer film itself and the solvent system in the hair spray composition. For these reasons, polymerization of maleic anhydride and methyl vinyl ether monomers was carried out using azo initiators at a suitable polymerization temperature. Specifically, to prepare a copolymer of maleic anhydride and methyl vinyl ether having a low weight average molecular weight of about 40,000 to about 70,000, and a polydispersity of about 1.8 to about 2.2, an azo initiator having a 10-hour half-life of about 60° to about 70° C. was used in an amount of about 1 to about 5% by weight of the maleic anhydride monomer present during the polymerization. The polymerization temperature was about 60° to about 90° C.

The polymerization step is followed by esterification of the copolymer obtained. The esterification step preferably is carried out in the absence of an esterification catalyst, e.g. an acid catalyst because it would remain in the esterified copolymer solution resulting in a hazy film when it is cast from hydroalcoholic solutions of high water content. Furthermore, an esterification catalyst also would cause diesterification as well as the desired monoesterification, which is undesirable because the diester is less water compatible than the half-ester. The diester also has a reduced Tg so that its fixative film is softer than the half-ester copolymer used in this invention.

If desired, the half-ester copolymer solution may be neutralized in an amount up to about 25 mole %. For this purpose, a suitable neutralizing agent, such as triisopropanol amine (TIPA), 3-aminopropanol (AMP-95), $NH_4OH$ or NaOH, and the like, may be used. In general, hair spray compositions of high water content require a higher degree of neutralization.

The invention will now be described in detail by reference to the following examples.

EXAMPLE 1

Preparation of the Ethyl Ester of a Maleic Anhydride-Methyl Vinyl Ether Copolymer in Ethanol (a) Copolymerization A pressurized reactor vessel was precharged with 7819 lbs of acetone and maintained at 70°–80° C. with agitation under a nitrogen atmosphere. Then separate streams of 5225 lbs of molten maleic anhydride (MA), 3713 lbs of liquid methyl vinyl ether (MVE) and a solution of 209 lbs. of 4,4'-azobis (4-cyanopentanoic acid) in 1033 lbs of acetone, (4% by weight based on MA) were introduced separately and continuously into the precharged reactor.

The MA addition rate was 15.47 lb/min; the MVE addition rate was 21.77 lb/min; and the initiator solution addition rate was 5.18 lb/min. The period of addition was 6 hours. The product was clear and odorless, viscous, 50% solids acetone solution of the maleic anhydride-methyl vinyl ether copolymer having a specific viscosity of about 0.3 and less. Residual monomers, acetone and maleic acid were substantially absent from the solution.

(b) Esterification and (c) Solvent Exchange

The copolymer solution (in acetone) then was esterified and solvent exchanged with ethanol by injecting vaporized ethanol at 85°–95° C. continuously through spargers below the surface of the solution over an 8 hour period while simultaneously distilling acetone overhead at atmospheric pressure at the boiling point of the solution (approximately 60° C.). The product was a crystal clear, odorless ethanol solution of the ethyl half-ester of the copolymer, at a 50% solids level, with less than 0.2% acetone therein, and substantially no residual monomers or maleic acid, at a specific viscosity of about 0.4 or less.

INVENTION COMPOSITIONS

Several innovative-type aerosol concentrates of the invention were prepared, as shown by the two specific examples in Table 1 below.

TABLE 1

Innovative Aerosol Hair Spray Concentrate

| Component | Percent by Wt. 80% VOC | Percent by Wt. 55% VOC |
|---|---|---|
| (a) Ester Copolymer of Invention | | |
| (Ex. 1) (MW 63,000) | 10.00 | 10.00 |
| (i) Aminomethyl Propanol AMP-95 | 0.44 | 0.18 |
| (b) SD 40 B Alcohol | 54.36 | 54.36 |
| (c) Water | — | 4.06 |
| (d) 152 A HFC propellant (a non-VOC) | 15.00 | 30.00 |

TABLE 1-continued

Innovative Aerosol Hair Spray Concentrate

| Component | Percent by Wt. 80% VOC | 55% VOC |
|---|---|---|
| Dimethyl Ether (a VOC) | 20.00 | 5.00 |
| (e) Others | | |
| Dimethicone Copolyol | 0.10 | 0.10 |
| Lauramide DEA | 0.10 | 0.10 |
| Ammonium Hydroxide | — | 0.10 |
| MEA Borate and MIPA Borate | — | 0.20 |
| Total: | 100.00% | 100.00% |

Restricter
Valve: Seaquist ST-74
Stem: 0.010"
Body: Capillary
Vapor Tap: 0.010"
ID Tubing: 0.030"
Actuator: ST-150 Misty
Orifice: 0.020"

PROPERTIES OF COPOLYMERS OF INVENTION

Table 2 summarizes the weight average molecular weights, polydispersity and specific viscosities for the ester copolymers used herein in comparison with other available prior art Gantrez® products. As can be seen from Table 2, the invention ester copolymers possess the lowest weight average molecular weight and lowest specific viscosity values, namely, 63,900 and 0.28, respectively, as compared to the other examples. The invention copolymer also possesses the narrowest polydispersity of 2.0.

TABLE 2

PHYSICAL PROPERTIES OF COPOLYMERS OF INVENTION AND COMPARATIVE COPOLYMERS

| Copolymer | Weight Average Molecular Wt,* $M_w$ | Polydispersity, $M_w/M_n$ | Specific Viscosity** |
|---|---|---|---|
| Invention (Example 1 herein) | 63,900 | 2.0 | 0.28 |
| Zamora (U.S. Pat. No. 5,233,367) | 82,700 | 3.2 | 0.35 |
| Goertz (U.S. Pat. No. 4,908,413) | 160,000 | 3.2 | 0.99 |

*based on polystyrene calibration curve
**1 wt. % solution of copolymer in ethanol The FIGURE is a plot of Brookfield viscosity of the concentrate of the invention vs. the percent solids therein, at various VOC levels. What is illustrated is that the viscosity of the concentrate follows a typical profile with an increased solids level, reaching the desired sprayable viscosity level of about 25 cps at about a 5–6% solids level when the IPC emission rate conforms to a (1) 55% VOC system. At (2) 80% VOC and (3) Anhydrous System levels, a greater solids content in the concentrate is required to achieve the same Brookfield viscosity, specifically 10% and above, respectively. Accordingly, such a suitably formulated concentrate, in cooperation with an appropriate restricter valve to control its spray rate can be used to deliver fixative particles at any desired VOC level under IPC regulations.

In high VOC hair spray systems, at 5% solutions, the viscosity of the polymer is too low resulting in a fine spray which does not coat the hair optimally. In essence, the formulation dries too quickly so the polymer does not have a chance to properly coat the hair fiber. This negative phenomenon is remedied herein by concentrating the solids to give an innovative product. This concentrate then approaches a low solids, low VOC system, however, without the negative of excess water present.

The aerosol concentrate of the invention exhibits the following advantageous use characteristics and properties, as shown in Table 3 below.

TABLE 3

| | |
|---|---|
| Film clarity | Clear film |
| Film hardness | 1 H to 9 H |
| pH | 6–9 |
| Long Term HHCR-90 min | >90% |
| Long Term HHCR-4 hr | >80% |
| Dry Time | <60 sec. |
| Duration of Tack | <40 sec. |
| Film character | Shiney |
| Spray Pattern | 2–4.5 in. |
| Spray particle size D[v,0.5] | 35–75μ |

The substantial absence of high molecular weight fractions in the copolymer of the invention also is advantageous because such fractions produces undesirable viscosity fluxes and negatively affect spray aesthetics. In addition, the low viscosity of high solids formulations of the copolymer solutions herein provides a stiffer hold characteristic for the user.

While the invention has been described with particular reference to certain embodiments thereof, it will be understood that changes and modifications may be made which are within the skill of the art. Accordingly, it is intended to be bound only by the following claims, in which:

What is claimed is:

1. An innovative aerosol hair spray concentrate which is capable of delivering an 80% or less volatile organic compound, and, in cooperation with a suitable restricter valve and actuator system, comprising, by weight, (a) about 5 to about 25% of the ethyl or butyl half-ester copolymer of maleic anhydride and methyl vinyl ether, having a weight average molecular weight of about 40,000 to about 70,000, optionally neutralized in an amount of up to about 25 mole %, wherein the copolymer has a polydispersity of about 1.8 to about 2.2, (b) about 40 to about 80% ethanol, (c) 0 to about 10% water, and (d) about 15 to about 40% propellant, said concentrate having a Brookfield viscosity of about 15 to about 30 cps.

2. A concentrate according to claim 1 wherein (a) is about 10 to about 20%.

3. A concentrate according to claim 1 which can deliver an 80% volatile organic compound spray, wherein (a) is 15%, (b) is 60%, (c) is 5%, and (d) is 20%.

* * * * *